US00PP33341P2

(12) United States Plant Patent
Masor

(10) Patent No.: US PP33,341 P2
(45) Date of Patent: Aug. 10, 2021

(54) ANGELONIA PLANT NAMED 'BALANGSPARPI'

(50) Latin Name: *Angelonia angustifolia*
Varietal Denomination: Balangsparpi

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/190,517

(22) Filed: Mar. 3, 2021

(51) Int. Cl.
*A01H 5/02* (2018.01)
*A01H 6/68* (2018.01)

(52) U.S. Cl.
USPC ..... Plt./404
CPC ..... *A01H 6/68* (2018.05)

(58) Field of Classification Search
USPC ..... Plt./404
CPC ..... A01H 6/68
See application file for complete search history.

*Primary Examiner* — Anne Marie Grunberg
(74) *Attorney, Agent, or Firm* — Audrey Charles

(57) ABSTRACT

A new and distinct cultivar of *Angelonia* plant named 'Balangsparpi', characterized by its dark purple-colored flowers, dark green-colored foliage, and moderately vigorous, prostrate-spreading growth habit, is disclosed.

1 Drawing Sheet

Latin name of genus and species of plant claimed: *Angelonia angustifolia.*

Variety denomination: 'Balangsparpi'.

BACKGROUND OF THE INVENTION

The present invention relates to a new and distinct cultivar of *Angelonia* plant botanically known as *Angelonia angustifolia* and hereinafter referred to by the cultivar name 'Balangsparpi'.

The new cultivar originated in a controlled breeding program in Arroyo Grande, Calif. during June 2017. The objective of the breeding program was the development of *Angelonia* cultivars having continuous flowering and a prostrate-spreading growth habit.

The new *Angelonia* cultivar is the result of self-pollination of the proprietary *Angelonia angustifolia* breeding selection coded ANG-07167-01, not patented, characterized by its medium purple-colored flowers, medium green-colored foliage, and moderately vigorous, semi-upright growth habit. The new cultivar was selected as a single flowering plant within the progeny of the above stated self-pollination during May 2018 in a controlled environment in Arroyo Grande, Calif.

Asexual reproduction of the new cultivar by terminal stem cuttings since May 2018 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balangsparpi' as a new and distinct cultivar of *Angelonia* plant:

1. Dark purple-colored flowers;
2. Dark green-colored foliage; and
3. Moderately vigorous, prostrate-spreading growth habit.

Plants of the new cultivar differ from plants of the parent primarily in having a more prostrate-spreading growth habit, darker purple-colored flowers and darker green-colored foliage.

Of the many commercially available *Angelonia* cultivars, the most similar in comparison to the new cultivar is ANGELMIST Spreading Bluebird 'Balangspird', U.S. Plant Pat. No. 29,260. However, in comparison, plants of the new cultivar differ from plants of 'Balangspird' in at least the following characteristics:

1. Plants of the new cultivar have more inflorescences per plant than plants of 'Balangspird'; and
2. Plants of the new cultivar have a dark purple petal color unlike the medium violet and white bicolored flowers of plants of 'Balangspird'.

In addition, the new cultivar can be compared to ANGELMIST Spreading Dark Purple 'Balangsparkl', U.S. Plant Pat. No. 25,558. However, in comparison, plants of the new cultivar differ from plants of 'Balangsparkl' in at least the following characteristics:

1. Plants of the new cultivar have a less violet-colored shade of flowers than plants of 'Balangsparkl'; and
2. Plants of the new cultivar have larger-sized corollas than plants of 'Balangsparkl'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balangsparpi'. The approximately 4-month-old plants were grown in 6-inch pots approximately 13 weeks in a greenhouse in West Chicago, Ill. Plants were given one pinch three weeks prior to transplant.

DETAILED BOTANICAL DESCRIPTION

Figure 1:
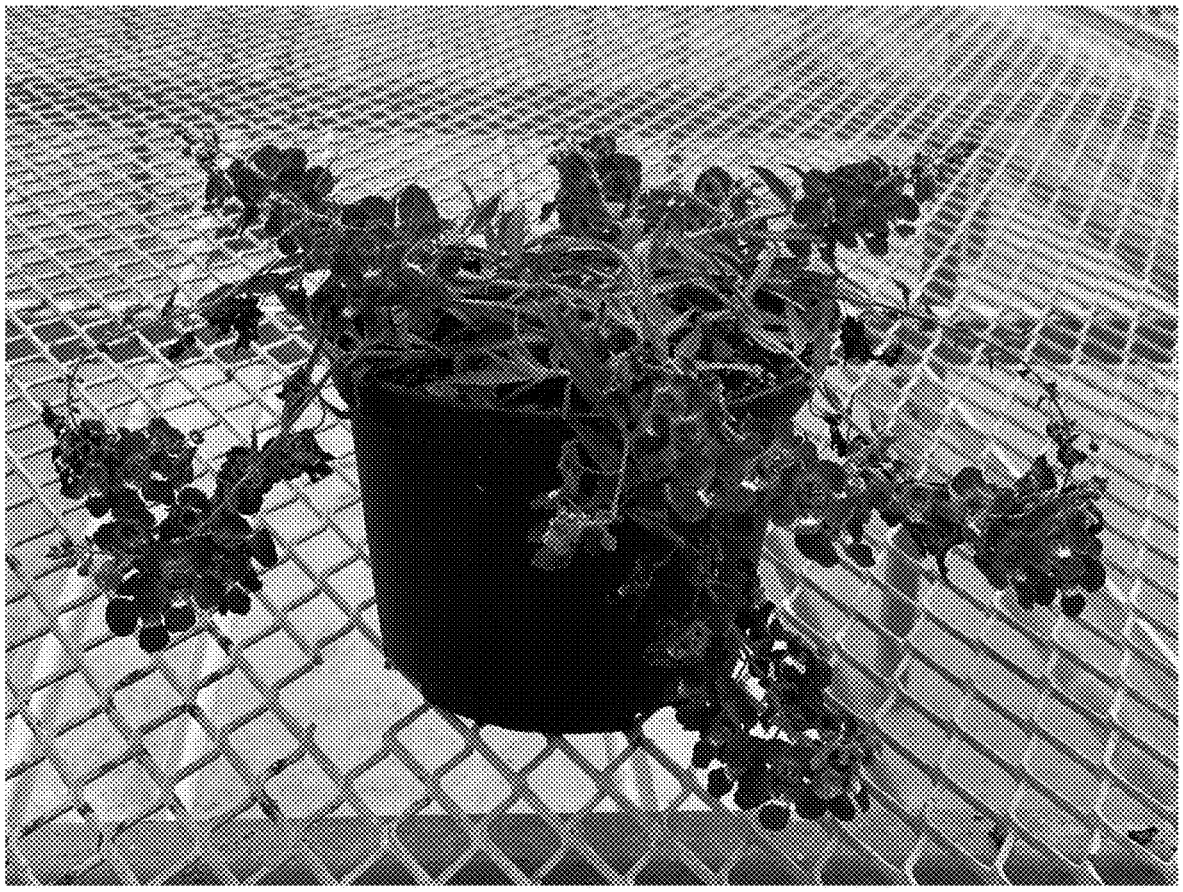
FIG. 1 illustrates a side view of the overall growth and flowering habit of 'Balangsparpi'.
Figure 2:
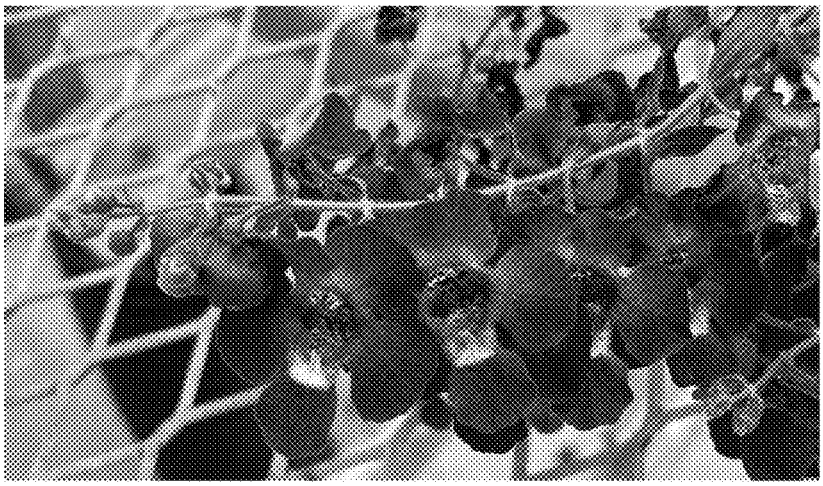
FIG. 2 illustrates a close-up view of an individual inflorescence of 'Balangsparpi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2021 under natural light conditions in Naperville, Ill.

The following descriptions and measurements describe approximately 4-month-old plants produced from cuttings from stock plants and grown in a glass-covered greenhouse under conditions comparable to those used in commercial practice. The plants were grown in West Chicago, Ill. in 6-inch pots for approximately 13 weeks utilizing a soilless growth medium. Plants were given one pinch three weeks prior to transplant. Greenhouse temperatures were maintained at approximately 70° F. to 75° F. (21° C. to 24° C.) during the day and approximately 68° F. to 74° F. (20° C. to 23° C.) during the night. Supplemental lighting was used. Measurements and numerical values represent averages of typical plants.

Botanical classification: *Angelonia angustifolia* 'Balangsparpi'.

Parentage:

*Female and male parent.*—Proprietary *Angelonia angustifolia* breeding selection coded ANG-07167-01, not patented.

Propagation:

*Type cutting.*—Terminal stem.

*Time to initiate roots.*—Approximately 7 to 9 days.

*Time to produce a rooted cutting.*—Approximately 21 to 28 days.

*Root description.*—Fine, fibrous.

*Rooting habit.*—Freely branching.

Plant description:

*Commercial crop time.*—Approximately 4 to 6 weeks from a rooted cutting to finish in a 10 cm pot.

*Growth habit and general appearance.*—Moderately vigorous, prostrate-spreading.

*Size.*—Height from soil level to top of plant plane: Approximately 8.0 cm. Width: Approximately 41.0 cm.

*Branching habit.*—Freely branching, pinching improves basal branching. Quantity of main branches per plant: Approximately 5.

*Branch.*—Shape: Square in cross section. Strength: Moderately strong, somewhat flexible. Length: Approximately 21.5 cm. Diameter: Approximately 2.5 mm. Length of central internode: Approximately 2.0 cm. Texture: Glabrous. Color of young and mature stems: 146B.

Foliage description:

*General description.*—Quantity of leaves per main branch: Approximately 14. Fragrance: None. Form: Simple. Arrangement: Opposite.

*Leaves.*—Aspect: Primarily perpendicular or obtuse angle to stem. Shape: Narrowly elliptic. Margin: Widely serrate. Apex: Acute. Base: Sessile. Venation pattern: Pinnate. Length of mature leaf: Approximately 4.5 cm. Width of mature leaf: Approximately 1.0 cm. Texture of upper and lower surfaces: Glabrous. Color of upper surface of young foliage: 137A with indistinguishable venation. Color of lower surface of young foliage: 137B with midvein of 146D, other venation indistinguishable. Color of upper surface of mature foliage: NN137A with indistinguishable venation. Color of lower surface of mature foliage: Closest to 137B with midvein of 146D, other venation indistinguishable.

Flowering description:

*Flowering habit.*—'Balangsparpi' is freely flowering under outdoor growing conditions with substantially continuous blooming from spring through autumn and year-round in greenhouse environment.

*Lastingness of individual flower on the plant.*—Approximately 7 to 10 days.

Inflorescence description:

*General description.*—Type: Terminal raceme. Quantity per plant: Approximately 11. Fragrance: Slight, sweet. Length: Approximately 10.0 cm. Width: Approximately 5.0 cm. Quantity of fully open flowers per inflorescence: Approximately 10.

Flower description:

*Type.*—Solitary, zygomorphic.

*Bud.*—Rate of opening: Generally takes 3 to 4 days for bud to progress from first color to fully open flower.

*Bud just before opening.*—Shape: Globular. Length: Approximately 6.0 mm. Diameter: Approximately 6.0 mm. Color of upper surface: 145A. Color of lower surface: 145C with 83D.

*Corolla.*—Shape: Bilabiate. Aspect: Facing outward. Length: Approximately 2.6 cm. Width: Approximately 2.5 cm. Depth: Approximately 9.0 mm.

*Petals.*—Quantity: 5 petals fused at base forming a throat and consisting of an upper lip with 2 petals and a lower lip with 3 petals, consisting of 2 lateral petals and one central petal. Shape: Obovate. Margin: Entire. Apex: Obtuse.

*Upper lip.*—Length of petals from throat: Approximately 8.0 mm. Width of each petal: Approximately 1.2 cm. Texture of upper surface: Moderately glandular pubescent. Gland color: 150C and colorless, transparent. Texture of lower surface: Glabrous. Color of upper surface when fully open: N81A and 83A to 83B with 83C at throat opening. Color of lower surface when fully open: 83B.

*Lower lip, lateral petals.*—Length of petals from throat: Approximately 9.0 mm. Width of each petal: Approximately 1.1 cm. Texture of upper surface: Moderately glandular pubescent. Gland color: 150C and colorless, transparent. Texture of lower surface: Densely glandular pubescent. Gland color: Colorless, transparent. Color of upper surface when fully open: N81A and 83A to 83B with 83C at throat opening. Color of lower surface when fully open: 83B to 83C.

*Lower lip, central petal.*—Length from the palate: Approximately 9.0 mm. Width: Approximately 1.0 cm. Texture of upper surface: Moderately glandular pubescent. Gland color: 150C and colorless, transparent. Texture of lower surface: Densely glandular pubescent. Gland color: 150C and colorless, transparent. Color of upper surface when fully open: N81A and 83A to 83B. Color of lower surface when fully open: 83B to 83C.

*Throat.*—Length: Approximately 8.0 mm. Width: Approximately: 7.0 mm. Texture of inner surface: Sparsely glandular pubescent. Gland color: 150C, transparent. Texture of outer surface: Glabrous. Color of inner surface: NN155D with and overlay of 83C and spots of N79A. Color of outer surface: 83D with spots of N79A. Palate color: 145D with spots of N79A and NN155D at lower lip. Palate texture: Sparsely glandular pubescent. Gland color: 150C, transparent. Teeth color: 83D.

*Calyx.*—Shape: Star, cupped. Diameter: Approximately 6.0 mm.

*Sepals.*—Quantity per flower: 5, fused at base. Shape: Ovate. Apex: Acute. Length: Approximately 3.0 mm. Width: Approximately 2.0 mm. Texture of upper (inner) surface: Sparsely glandular pubescent. Texture of lower (outer) surface: Densely glandular pubescent. Gland color: Colorless, transparent. Color of upper (inner) surface: 137A. Color of lower (outer) surface: 137A with an overlay of 187A.

*Pedicel.*—Strength: Strong, flexible. Aspect: Acute angle to stem. Length: Approximately 1.1 cm. Diameter: Approximately 1.0 mm. Texture: Densely glandular pubescent. Gland color: Colorless, transparent. Color: 146B.

*Reproductive organs.*—Androecium: Stamen quantity: 4 per flower. Filament length: Approximately 3.0 mm. Filament texture: Sparsely glandular pubescent. Gland color: Colorless, transparent. Filament color: NN155D faintly tinted with 83D. Anther shape: Bilobed. Anther length: Approximately 1.0 mm. Anther color: 103D. Pollen amount: Abundant. Pollen color: 155D. Gynoecium: Pistil quantity: 1 per flower. Pistil length: Approximately 5.0 mm. Stigma shape: Pointed. Stigma length: Less than 1.0 mm. Stigma color: 83A. Style length: Approximately 4.0 mm. Style color: NN155D faintly tinted with 83D. Ovary diameter: Approximately 1.0 mm. Ovary texture: Sparsely glandular pubescent. Gland color: Colorless, transparent. Ovary color: 146D.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balangsparpi', substantially as herein illustrated and described.

* * * * *